US011589756B2

(12) United States Patent
Geheb et al.

(10) Patent No.: US 11,589,756 B2
(45) Date of Patent: Feb. 28, 2023

(54) PROCESSING IMPEDANCE SIGNALS FOR BREATH DETECTION

(71) Applicant: ZOLL Medical Corporation, Chelmsford, MA (US)

(72) Inventors: Frederick J Geheb, Lenexa, KS (US); Gary A Freeman, Waltham, MA (US); Ulrich Herken, Medford, MA (US)

(73) Assignee: ZOLL Medical Corporation, Chelmsford, MA (US)

( * ) Notice: Subject to any disclaimer, the term of this patent is extended or adjusted under 35 U.S.C. 154(b) by 661 days.

(21) Appl. No.: 16/717,153

(22) Filed: Dec. 17, 2019

(65) Prior Publication Data

US 2020/0121196 A1 Apr. 23, 2020

Related U.S. Application Data

(63) Continuation of application No. 15/910,038, filed on Mar. 2, 2018, now Pat. No. 10,548,486, which is a
(Continued)

(51) Int. Cl.
*A61B 5/0205* (2006.01)
*A61B 5/08* (2006.01)
(Continued)

(52) U.S. Cl.
CPC .......... *A61B 5/0205* (2013.01); *A61B 5/0809* (2013.01); *A61B 5/11* (2013.01);
(Continued)

(58) Field of Classification Search
None
See application file for complete search history.

(56) References Cited

U.S. PATENT DOCUMENTS 3,991,304 A 11/1976 Hillsman
4,059,099 A 11/1977 Davis
(Continued)

FOREIGN PATENT DOCUMENTS

CN 1613097 5/2005
CN 101296730 10/2008
(Continued)

OTHER PUBLICATIONS

Aase et al. CPR Artifact Removal from Human ECG Using Optimal Multichannel Filtering, 2000, IEE Transactions on Biomedical Engineering, vol. 47, No. 11, 1440-1449.
(Continued)

*Primary Examiner* — Michael R Bloch
(74) *Attorney, Agent, or Firm* — ZOLL Medical Corporation

(57) ABSTRACT

An apparatus for assisting in providing patient ventilations includes electrodes configured to provide airflow activities signals, chest compression sensors configured to provide chest displacement signals due to chest compressions, a processor and a memory configured to receive the airflow activities and chest displacement signals, identify a presence of chest compressions based on the chest displacement signals, subsequently confirm an absence of chest compressions applied to the patient based on the chest displacement signals, adjust signal processing parameters for the airflow activities signals in response to the confirmed absence of chest compressions, and process the airflow activities signals using the adjusted signal processing parameters to determine feedback for providing the patient ventilations in the absence of chest compressions, and an output device coupled to the processor and the memory and configured to provide the ventilation feedback.

15 Claims, 6 Drawing Sheets

Related U.S. Application Data continuation of application No. 14/200,571, filed on Mar. 7, 2014, now Pat. No. 9,968,267.

(60) Provisional application No. 61/791,150, filed on Mar. 15, 2013.

(51) Int. Cl.
  *A61B 5/11* (2006.01)
  *A61B 5/00* (2006.01)

(52) U.S. Cl.
  CPC ............ *A61B 5/6823* (2013.01); *A61B 5/725* (2013.01); *A61B 5/74* (2013.01); *A61B 5/742* (2013.01); *A61B 5/7405* (2013.01); *A61B 2562/0219* (2013.01)

(56) References Cited

U.S. PATENT DOCUMENTS

| | | |
|---|---|---|
| 4,088,138 A | 5/1978 | Diack et al. |
| RE30,372 E | 8/1980 | Mirowski et al. |
| 4,296,755 A | 10/1981 | Judell |
| 4,355,634 A | 10/1982 | Kanter |
| 4,588,383 A | 5/1986 | Parker et al. |
| 4,610,254 A | 9/1986 | Morgan et al. |
| 4,619,265 A | 10/1986 | Morgan et al. |
| 4,680,708 A | 7/1987 | Ambos et al. |
| 4,781,200 A | 11/1988 | Baker |
| 4,928,674 A | 5/1990 | Halperin et al. |
| 5,077,667 A | 12/1991 | Brown et al. |
| 5,092,341 A | 3/1992 | Kelen |
| 5,109,862 A | 5/1992 | Kelen et al. |
| 5,247,945 A | 9/1993 | Heinze et al. |
| 5,285,792 A | 2/1994 | Sjoquist et al. |
| RE34,800 E | 11/1994 | Hutchins |
| 5,391,187 A | 2/1995 | Freeman |
| 5,439,483 A | 8/1995 | Duong-Van |
| 5,466,244 A | 11/1995 | Morgan |
| 5,471,991 A | 12/1995 | Shinnar |
| 5,474,574 A | 12/1995 | Payne et al. |
| 5,496,257 A | 3/1996 | Kelly |
| 5,511,553 A | 4/1996 | Segalowitz |
| 5,562,710 A | 10/1996 | Olsen et al. |
| 5,589,639 A | 12/1996 | D'Antonio et al. |
| 5,591,213 A | 1/1997 | Morgan |
| 5,611,815 A | 3/1997 | Cole et al. |
| 5,617,853 A | 4/1997 | Morgan |
| 5,619,265 A | 4/1997 | Suzuki et al. |
| 5,645,571 A | 7/1997 | Olson et al. |
| 5,662,690 A | 9/1997 | Cole et al. |
| 5,683,424 A | 11/1997 | Brown et al. |
| 5,700,281 A | 12/1997 | Brewer et al. |
| 5,735,879 A | 4/1998 | Gliner et al. |
| 5,755,671 A | 5/1998 | Albrecht et al. |
| 5,957,856 A | 9/1999 | Weil et al. |
| 5,967,995 A | 10/1999 | Shusterman et al. |
| 6,125,299 A | 9/2000 | Groenke et al. |
| 6,171,257 B1 | 1/2001 | Weil et al. |
| 6,174,295 B1 | 1/2001 | Cantrell et al. |
| 6,178,357 B1 | 1/2001 | Gliner et al. |
| 6,188,928 B1 | 2/2001 | Noren et al. |
| 6,224,562 B1 | 5/2001 | Lurie et al. |
| 6,246,907 B1 | 6/2001 | Lin et al. |
| 6,263,238 B1 | 7/2001 | Brewer et al. |
| 6,269,267 B1 | 7/2001 | Bardy et al. |
| 6,273,088 B1 | 8/2001 | Hillsman |
| 6,289,243 B1 | 9/2001 | Lin et al. |
| 6,306,107 B1 | 10/2001 | Myklebust et al. |
| 6,308,094 B1 | 10/2001 | Shusterman et al. |
| 6,351,671 B1 | 2/2002 | Myklebust et al. |
| 6,360,125 B1 | 3/2002 | Weil et al. |
| 6,390,996 B1 | 5/2002 | Halperin et al. |
| 6,393,316 B1 | 5/2002 | Gillberg et al. |
| 6,418,342 B1 | 7/2002 | Owen et al. |
| 6,427,685 B1 | 8/2002 | Ray, II |
| 6,438,419 B1 | 8/2002 | Callaway et al. |
| 6,480,734 B1 | 11/2002 | Zhang et al. |
| 6,496,731 B1 | 12/2002 | Lovett |
| 6,553,257 B2 | 4/2003 | Snyder et al. |
| 6,597,943 B2 | 7/2003 | Taha et al. |
| 6,622,042 B1 | 9/2003 | Thacker |
| 6,658,290 B1 | 12/2003 | Lin et al. |
| 6,671,545 B2 | 12/2003 | Fincke |
| 6,687,540 B2 | 2/2004 | Marcovecchio |
| 6,807,442 B1 | 10/2004 | Myklebust et al. |
| 6,827,695 B2 | 12/2004 | Palazzolo et al. |
| 6,865,413 B2 | 3/2005 | Halperin et al. |
| 6,980,112 B2 | 12/2005 | Nee |
| 6,990,373 B2 | 1/2006 | Jayne et al. |
| 7,013,176 B2 | 3/2006 | Ding et al. |
| 7,056,295 B2 | 6/2006 | Halperin |
| 7,074,199 B2 | 7/2006 | Halperin et al. |
| 7,108,665 B2 | 9/2006 | Halperin et al. |
| 7,242,979 B1 | 7/2007 | Kelly et al. |
| 7,469,697 B2 | 12/2008 | Lee et al. |
| 7,630,762 B2 | 12/2009 | Sullivan et al. |
| 7,747,319 B2 | 6/2010 | Freeman |
| 8,192,367 B2 | 6/2012 | Myklebust et al. |
| 8,315,693 B2 | 11/2012 | Lu et al. |
| 8,844,525 B2 | 9/2014 | Schindhelm et al. |
| 9,364,625 B2 | 6/2016 | Silver et al. |
| 9,539,434 B2 | 1/2017 | Sullivan |
| 2001/0047140 A1 | 11/2001 | Freeman |
| 2002/0165585 A1 | 11/2002 | Dupelle et al. |
| 2003/0060723 A1 | 3/2003 | Joo et al. |
| 2005/0101889 A1* | 5/2005 | Freeman .............. A61H 31/007 601/41 |
| 2005/0256415 A1 | 11/2005 | Tan et al. |
| 2006/0011203 A1 | 1/2006 | Myklebust |
| 2006/0025825 A1* | 2/2006 | Bowers ................. A61B 5/721 607/5 |
| 2006/0270952 A1 | 11/2006 | Freeman et al. |
| 2007/0032830 A1 | 2/2007 | Bowers |
| 2007/0060785 A1 | 3/2007 | Freeman et al. |
| 2007/0135726 A1* | 6/2007 | Ye ........................ A61B 5/0809 600/529 |
| 2007/0169779 A1 | 7/2007 | Freeman |
| 2007/0219588 A1 | 9/2007 | Freeman |
| 2010/0256539 A1 | 10/2010 | Strand et al. |
| 2011/0202100 A1* | 8/2011 | Tan ........................ G16H 20/30 607/6 |
| 2011/0284004 A1* | 11/2011 | Silver ............... A61M 16/0003 128/205.13 |
| 2012/0010543 A1 | 1/2012 | Johnson et al. |
| 2012/0302910 A1 | 11/2012 | Freeman et al. |
| 2013/0060315 A1 | 3/2013 | Elghazzawi et al. |
| 2013/0282069 A1* | 10/2013 | Thiagarajan ......... A61N 1/3993 607/3 |

FOREIGN PATENT DOCUMENTS

| | | |
|---|---|---|
| CN | 101626797 | 1/2010 |
| JP | 2007195977 | 8/2007 |
| JP | 2007244879 | 9/2007 |
| WO | 2002078775 | 10/2002 |

OTHER PUBLICATIONS

Barash et al., "Novel Technology to Limit Chest Compression Interruption with Experienced Advanced Life Support Providers," American Heart Association Abstract p. 65, Circulation 2009, 120:S1455.

Geheb, A system for the determination of ventricular tachycardia or ventricular fibrillation during cardiopulmonary resuscitation, Apr. 2002, 2 pages.

Li et al., "Identifying potentially shockable rhythms without interrupting cardiopulmonary resuscitation," Critical Care Medicine 36(1):198-203(2008).

Lloyd et al., "Hands-On Defibrillation. An Analysis of Electrical Current Flow Through Rescuers in Direct Contact with Patients During Biphasic External Defibrillation," Journal of the American Heart Association Circulation 117:2510-2514 (2008).

(56) References Cited

OTHER PUBLICATIONS

Povoas et al., "Predicting the success of defibrilation by electrocardiographic analysis," Resuscitation 53:77-82 (2002).
Robertson et al., "Defibrillator Charging During On-Going Chest Compressions: A Multi-Center Study of In-Hospital Resuscitation," American Heart Association Abstract 2644, Circulation 2009, 120(18)2:S670.
Ruiz de Gauna et al., "A method to remove CPR artefacts from human ECG using only the recorded ECG," Resuscitation 76:271-278(2008).
Silver et al., "A New Defibrillator Mode Reduces Chest Compression Interruptions for Lay Rescuers and BLS Providers," American Heart Association Abstract p. 173, Circulation 2009, 120:S1479.
Sullivan et al., "How Much Can Hands-off Time Be Reduced by Performing Rhythm Analysis During CPR?" American Heart Association Abstract p. 176, Circulation 2009,120:51479.
Yu et al., "The resuscitation blanket: A useful tool for "hands-on" defibrillation," Resuscitation 81:230-235 (2010).

\* cited by examiner

PROCESSING IMPEDANCE SIGNALS FOR BREATH DETECTION

CLAIM OF PRIORITY

This application is a continuation under 35 U.S.C. § 120 of U.S. patent application Ser. No. 15/910,038, filed on Mar. 2, 2018, which is a continuation of U.S. patent application Ser. No. 14/200,571, filed on Mar. 7, 2014 and issued as U.S. Pat. No. 9,968,267, which claims priority under 35 USC § 119(e) to U.S. Patent Application Ser. No. 61/791,150, filed on Mar. 15, 2013. All subject matter set forth in the above referenced applications is hereby incorporated by reference in its entirety into the present application as if fully set forth herein.

TECHNICAL FIELD

This document relates to processing signals from a patient's chest for breath detection, and in particular to systems and techniques for processing signals to monitor ventilation of the patient during cardio-pulmonary resuscitation (CPR) treatment.

BACKGROUND

Sudden cardiac arrest (colloquially "heart attack") is a frequent cause of death. One treatment for cardiac arrest is quick and competent chest compressions to keep blood flowing through a patient's heart. Along with chest compressions, a rescuer may ventilate the patient by either exhaling into the patient's mouth or nose or utilizing a device that pushes air into the patient's lungs. Rescuers, in particular untrained rescuers, may experience a rush of excitement during such medical emergencies that can result in over-ventilating the patient. Such untrained rescuers may consider such additional ventilations as being helpful to the patient; however, studies have shown the opposite. Additional cycles of inflating and deflating the patient's lungs may raise pressure in the patient's chest causing circulation of the patient's blood to actually decrease. As a result, the ability to monitor ventilations and provide CPR in a competent manner can be a very important personal skill, and is particularly important for professional healthcare workers such as emergency medical technicians (EMTs).

SUMMARY

This document describes systems and techniques for processing signals representative of airflow activities (e.g., ventilation, respiration, etc.) of a patient during CPR treatment. By accounting for signal artifacts that represent the motion of chest compressions applied during CPR, a processed signal may be produced that more accurately represents the airflow activities of the patient, in particular identifying the occurrences of ventilations. Based on this information, feedback can be provided to the rescuer, for example, to appropriately adjust the CPR treatment being applied to the patient such as reducing ventilation frequency so not to overly hinder blood circulation.

In one aspect, an apparatus includes a computing device that includes a memory configured to store instructions. The computing device also includes a processor to execute the instructions to perform operations that include receiving a signal representative of electrical impedance in a chest of a patient, and, receiving a signal representative of the motion of chest compressions performed on the patient during a cardiopulmonary resuscitation (CPR) treatment. The operations also include processing the received signal representative of the motion of chest compressions to determine one or more characteristics of the motion, and, processing the received signal representative of the electrical impedance to determine parameters relevant to a production of a signal representative of airflow activities of the patient. Operations also include modifying the one or more determined parameters based on the one or more determined characteristics of the motion to produce the signal representative of airflow activities of the patient.

Implementations may include one or more of the following features. The computing device may be capable of providing a feedback signal reflective of the airflow activities for adjusting the CPR treatment of the patient. The one or more determined parameters may include filtering parameters for processing the received signal representative of the electrical impedance. The one or more determined parameters may include one or more thresholds for processing the received signal representative of the electrical impedance. The determined one or more characteristics of the received signal representative of the motion of chest compressions may reflect an absence of chest compressions being performed on the patient over a period of time. The determined one or more characteristics of the received signal representative of the motion of chest compressions may represent the timing of chest compression occurrences. Modifying the one or more parameters may be performed in multiple instances for adjusting the processing of the received signal representative of the electrical impedance to reflect changes in the chest compressions. The signal representative of electrical impedance in the chest of the patient may be provided by a plurality of defibrillator electrode pads. The signal representative of the motion of the chest compressions may be provided by an accelerometer positioned to move in coordination with the motion of the patient's chest. The signal representative of the motion of the chest compressions may be an electrocardiogram signal from the patient.

In another aspect, one or more computer readable media storing instructions that are executable by a processing device, and upon such execution cause the processing device to perform operations including receiving a signal representative of electrical impedance in a chest of a patient, and, receiving a signal representative of the motion of chest compressions performed on the patient during a cardiopulmonary resuscitation (CPR) treatment. Operations also include processing the received signal representative of the motion of chest compressions to determine one or more characteristics of the motion, and, processing the received signal representative of the electrical impedance to determine parameters relevant to a production of a signal representative of airflow activities of the patient. Operations also include modifying the one or more determined parameters based on the one or more determined characteristics of the motion to produce the signal representative of airflow activities of the patient.

Implementations may include one or more of the following features. The computing device may be capable of providing a feedback signal reflective of the airflow activities for adjusting the CPR treatment of the patient. The one or more determined parameters may include filtering parameters for processing the received signal representative of the electrical impedance. The one or more determined parameters may include one or more thresholds for processing the received signal representative of the electrical impedance. The determined one or more characteristics of the received signal representative of the motion of chest compressions may reflect an absence of chest compressions being performed on the patient over a period of time. The determined one or more characteristics of the received signal representative of the motion of chest compressions may represent the timing of chest compression occurrences. Modifying the one or more parameters may be performed in multiple instances for adjusting the processing of the received signal representative of the electrical impedance to reflect changes in the chest compressions. The signal representative of electrical impedance in the chest of the patient may be provided by a plurality of defibrillator electrode pads. The signal representative of the motion of the chest compressions may be provided by an accelerometer positioned to move in coordination with the motion of the patient's chest. The signal representative of the motion of the chest compressions may be an electrocardiogram signal from the patient.

In another aspect, a computing device implemented method includes receiving a signal representative of electrical impedance in a chest of a patient, and, receiving a signal representative of the motion of chest compressions performed on the patient during a cardiopulmonary resuscitation (CPR) treatment. The method also includes processing the received signal representative of the motion of chest compressions to determine one or more characteristics of the motion, and, processing the received signal representative of the electrical impedance to determine parameters relevant to a production of a signal representative of airflow activities of the patient. The method also includes modifying the one or more determined parameters based on the one or more determined characteristics of the motion to produce the signal representative of airflow activities of the patient.

Implementations may include one or more of the following features. The computing device may be capable of providing a feedback signal reflective of the airflow activities for adjusting the CPR treatment of the patient. The one or more determined parameters may include filtering parameters for processing the received signal representative of the electrical impedance. The one or more determined parameters may include one or more thresholds for processing the received signal representative of the electrical impedance. The determined one or more characteristics of the received signal representative of the motion of chest compressions may reflect an absence of chest compressions being performed on the patient over a period of time. The determined one or more characteristics of the received signal representative of the motion of chest compressions may represent the timing of chest compression occurrences. Modifying the one or more parameters may be performed in multiple instances for adjusting the processing of the received signal representative of the electrical impedance to reflect changes in the chest compressions. The signal representative of electrical impedance in the chest of the patient may be provided by a plurality of defibrillator electrode pads. The signal representative of the motion of the chest compressions may be provided by an accelerometer positioned to move in coordination with the motion of the patient's chest. The signal representative of the motion of the chest compressions may be an electrocardiogram signal from the patient.

The details of one or more embodiments are set forth in the accompanying drawings and the description below. Other features and advantages will be apparent from the description and drawings, and from the claims.

DESCRIPTION OF DRAWINGS

Like reference symbols in the various drawings indicate like elements.

DETAILED DESCRIPTION

Figure 1:
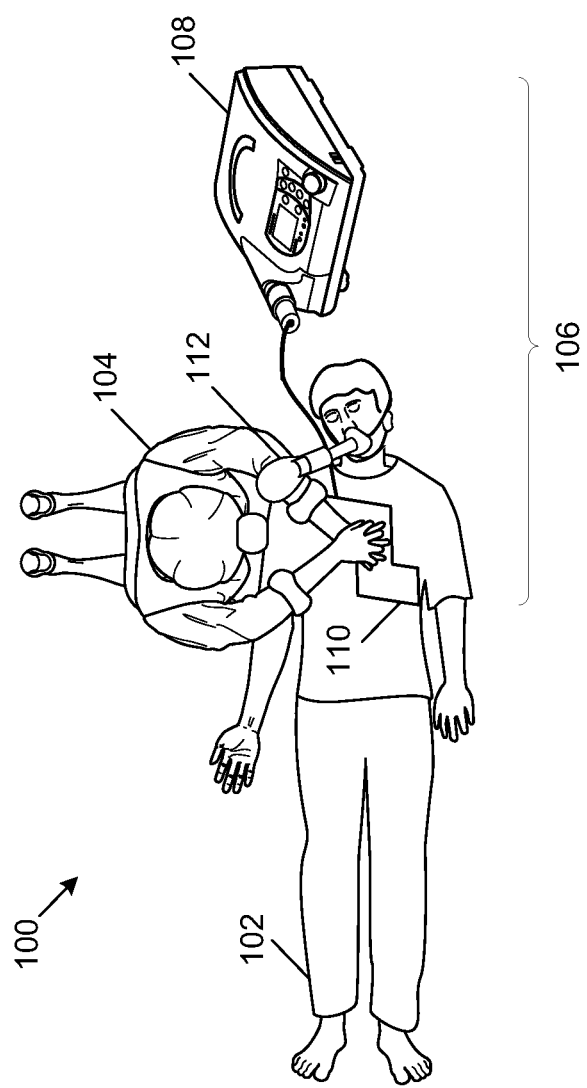
FIG. 1 illustrates a caregiver using a system for responding to an emergency medical condition.

Referring to FIG. 1, at a rescue scene 100, a caregiver 104 performs cardiopulmonary resuscitation (CPR) on a victim or patient 102 (the terms are used interchangeably here to indicate a person who is the subject of intended or actual CPR and related treatment, or other medical treatment), such as an individual who has apparently undergone sudden cardiac arrest. The caregiver 104 may be, for instance, a civilian responder with limited or no training in lifesaving techniques; a first responder, such as an emergency medical technician (EMT), police officer, or firefighter; or a medical professional, such as a physician or nurse. The caregiver 104 may be acting alone or may be acting with assistance from one or more other caregivers, such as a partner EMT.

In this illustration, the caregiver 104 can deploy a self-contained response unit 106 for use with an electronic defibrillating system including a defibrillator, such as an automated external defibrillator (AED) 108, a professional defibrillator, or another type of defibrillating apparatus. The AED 108 may take a variety of forms, such as the ZOLL MEDICAL R Series, E Series, or X Series defibrillators. In this example, the response unit 106 includes an assembly of electrode pads 110 through which the AED 108 can provide defibrillation to the patient 102. The response unit 106 also includes one or more sensors that provide signals to the AED 108, based on which the AED 108 can instruct the caregiver 104 in performing CPR. For example, the electrical impedance present in the chest of the patient 102 may be measured between the electrode pads of the assembly 110 and provided in a signal to the AED 108. Such an impedance signal may be used for a variety of operations of the AED 108, for example, based upon the measured impedance, the AED 108 may adjust the amount of current applied to the victim's heart during defibrillation (e.g., high impedance may call for an increased current level). The impedance across the patient's chest can also be used to detect the airflow activities (e.g., respiration, ventilation, etc.) of the victim. As the patient's lungs expand and contract, the geometry of the patient's chest changes that causes the measured impedance to correspondingly change.

The electrode pad assembly 110 may also include one or more sensors for collecting other signals and sensing other phenomena. For example, the electrode pad assembly 110 may include one or more sensors for collecting electrocardiogram (ECG) signals read from the patient 102. The assembly of electrode pads 110 may also include one or more sensors measuring chest compressions applied to the patient 102. For example, a sensor may be positioned in a location where the caregiver 104 is to place the palms of their hands when performing CPR chest compressions on the patient. As a result, the sensor may move with the victim's chest and the caregiver's hands, and provide a measure of the vertical displacement of such motion.

In this example, the self-contained response unit 106 also includes a ventilation bag 112, shown sealed around the mouth of the victim 102. The ventilation bag 112 may, for the most part, takes a familiar form, and may include a flexible body structure that the caregiver 104 may squeeze periodically to provide ventilation on the patient 102 when the patient is not breathing sufficiently on his or her own.

As mentioned above, over ventilating the patient 102 (e.g., due to an overly-excited novice caregiver), may cause a variety of repercussions. For example, inflating the victim's lungs too frequently may result in excess pressure being placed on the victim's heart that can prevent an accurate supply of blood from being provided to the heart and circulated throughout the patient's body. As such, monitoring the ventilations being applied to the victim and providing the caregiver 104 feedback regarding the ventilations (e.g., inform the caregiver to reduce the frequency of ventilations, etc.) may be crucial for the patient's blood circulation.

Figure 2:
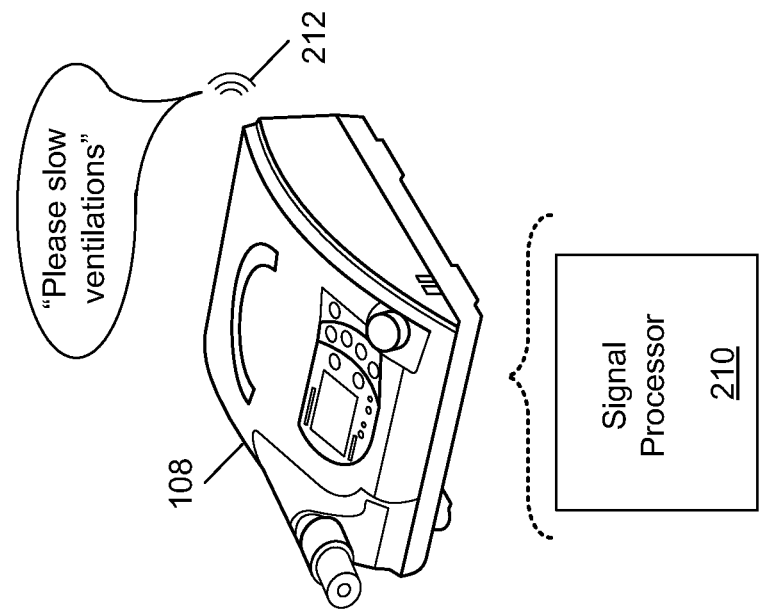
FIG. 2 illustrates signals used for detecting airflow activities of a patient.
Figure 2:
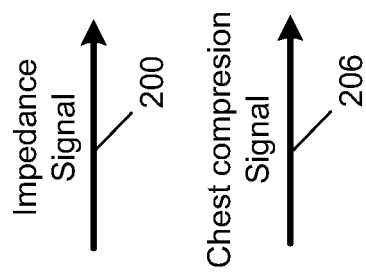
Figure 2:
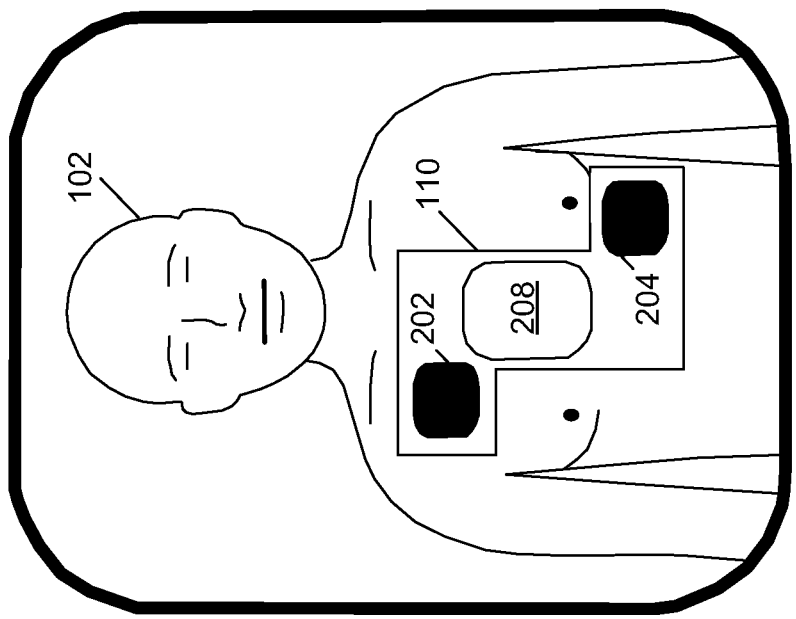

Referring to FIG. 2, one or more techniques may be implemented for attaining a measure of the ventilations being applied to the patient 102 or other types of airflow activities associated with the patient (e.g., unassisted inhaling and exhaling of the patient, etc.). For example, an impedance signal measured across the chest of the patient 102 may be processed for representing airflow activities (e.g., ventilations, unassisted breathing by the patient, etc.) and to determine if the patient is being over ventilated. As illustrated in the figure, a representation of the upper portion of the victim 102 is illustrated to present the deployed assembly of electrode pads 110. Two signals are illustrated as being provided to the AED 108 from the assembly of electrode pads 110. In particular, an impedance signal (graphically represented by arrow 200) is provided to the AED 108. In this particular arrangement, the impedance signal is provided by passing electrical current between two electrodes 202, 204, however, other techniques may be employed for measuring electrical impedance across the patient's chest. Also, different types of electrode configurations may be implemented. For example, more than two electrodes may be used in some arrangements for measuring the impedance present in the patient's chest.

In general, the level of impedance represented by the impedance signal 200 varies as the geometry of patient's chest changes due to the volume of air introduced by the ventilation bag 112 (shown in FIG. 1). By detecting the corresponding change in the impedance signal, a substantially accurate count of the ventilations may be determined along with other associated characteristics (e.g., ventilation rate, etc.). However, often other activities associated with the CPR treatment being applied to the victim may influence or even corrupt the impedance signal and thereby affect the accuracy of the ventilation count determined by the AED 108. For example, chest compressions performed by the caregiver 104 may also cause a change in the geometry of the patient's chest and corresponding cause electrical impedance fluctuations. Since changes in the impedance signal may also reflect chest compressions, the signal may not provide an accurate measure of the ventilations applied to the patient 102 and the AED may incorrectly determine that the patient is being over ventilated, or possibly worse, that the patient is being properly ventilated when in actuality the patient is being over ventilated.

One or more techniques and methodologies may be implemented to address the potentially corrupting influences on the impedance signal by the chest compressions applied by the caregiver 104. For example, the impedance signal provided by the assembly of electrode pads 110 may be processed to account for the applied chest compressions. In this particular example, a signal (graphically represented by the arrow 206) is provided to the AED 108 that represents the applied chest compressions. By using this chest compression signal, the AED 108 may process the impedance signal to substantially remove artifacts included in the impedance signal that represent the chest compressions and thereby provide a more accurate count of the ventilations applied to the patient 102.

One or more techniques may be implemented for producing a signal representative of chest compressions applied to a patient. For example, the assembly of electrode pads 110 may also include a center portion at which an accelerometer assembly 208 is mounted. The accelerometer assembly 208 may include a housing inside which is mounted an accelerometer sensor configuration. The accelerometer assembly 208 may be positioned in a location where the caregiver 104 is to place the palms of their hands when performing CPR chest compressions on the patient 102. As a result, the accelerometer assembly 208 may move with the patient's 102 chest and the caregiver's hands, and acceleration of such movement may be double-integrated to identify a vertical displacement of such motion. In some arrangements the accelerometer assembly 208 may include two or more accelerometer that may be used in concert to provide the chest compression signal (e.g., provide an averaged signal from the multiple sensors) to the AED 108. Further, other types of technology may be employed alone or in combination (e.g., in concert with the accelerometer assembly 208) to produce a signal representative of chest compressions. For example, one or more pressure sensors, ultrasound technology, string gauges, laser interferometry, magnetic field technology, cameras, etc. may be implemented for providing chest compression signals. Different types of signals may also be used for attaining information representative of chest compressions. For example, one or more ECG signals collected from a patient (e.g., by the electrode pad assembly 110) may be used for identifying chest compression during CPR treatment. In some arrangements, the impedance signal (or another impedance signal may be used for identifying chest compressions).

Provided the impedance signal 200 and the chest compression signal 206, the AED 108 may implement one or more techniques to process the signals to identify airflow activities of the patient 102 such as occurrences of ventilations, unassisted respiratory activities, etc. As illustrated in the figure, the AED 108 includes a signal processor 210 that processes the provided signals. The signal processor 210 may be software based (e.g., one or more processes, routines, operations, functions, etc.), hardware based (e.g., one or more general processing units, specialized processing units, etc.), implemented in software and hardware, etc. In addition to using the information provided by the signals (e.g., the impedance signal, chest compression signal, etc.), the signal processor 210 may also use information from other sources, for example, locally stored data (e.g., stored in one or more memories in the AED 108), data stored external to the AED (e.g., in one or more remote memories that may or may not be network accessible), etc. By processing the received signals, and potentially using other information, the signal processor 210 may initiate the production of one or more signals for alerting the caregiver 104. For example, one or more feedback signals (e.g., an audible alert signal 212) may be produced and provided to the caregiver 104 for initiating appropriate action (e.g., reduce the frequency of ventilations applied to the patient). Other types of feedback signals may also be initiated by the signal processor 210. For example, visual signals provided from a series of light emitting diodes (LEDs), one or more graphical displays, etc. may be used for providing feedback (e.g., alerts, instructions, etc.) to the caregiver 104.

One or more techniques may be implemented by the signal processor 210 to produce a signal that represents ventilations of the patient 102 or other types of airflow activities associated with the patient. For example, the chest compression signal 206 may be used to determine one or more characteristics associated with the chest motion (e.g., compression depth, timing, rate, etc.). The impedance signal may be used to determine one or more parameters (e.g., filtering parameters, thresholds, etc.) relevant for producing a signal representative of airflow activities of the patient. Once determined, parameters may be modified (e.g., cutoff frequency changed, thresholds increased or decreased, etc.) for processing the impedance signal 200 to substantially remove artifacts present in the impedance signal that correspond to the performed chest compressions. By removing the artifacts due to the chest compressions, the processed impedance signal may be more representative of airflow activities such as ventilations and less likely of representing geometry changes of the victim's chest due to applied compressions. For one potential processing technique, particular parameters may be identified by the signal processor 210 from the chest compression signal 206. For example, one or more filtering parameters (e.g., filter coefficients, cut off frequencies, etc.) may be identified from the chest compression signal, appropriately modified, and used to filter the impedance signal. Other parameters may also be identified, for example, one or more threshold values may be identified and used to define the occurrence of individual ventilations (or other types of airflow activities) from the impedance signal 200. In some implementations parameters may be determined for other types of airflow activities.

In addition to determining and using such parameters for processing the impedance signal, the parameters may be adjusted over time. For example, filtering and threshold parameters may be adjusted based upon changes in chest compressions being applied to the victim. As such, the processing of the impedance signal may be considered adaptive to changes in the applied chest compressions. Parameters may also be determined based upon no chest compressions being detected. For example, if determined that no compressions are being applied (e.g., from the chest compression signal 206) over a period of time (e.g., a few seconds), parameters for processing the impedance signal may be changed (e.g., change filter coefficients, threshold levels, etc.). With compressions absent, the impedance signal can be considered less corrupted and processing to account for compressions can be downplayed. Once compressions reappear (or newly appear) and are detected, the parameters may be adjusted again to account for the influences of the compressions in the impedance signal.

Figure 3:
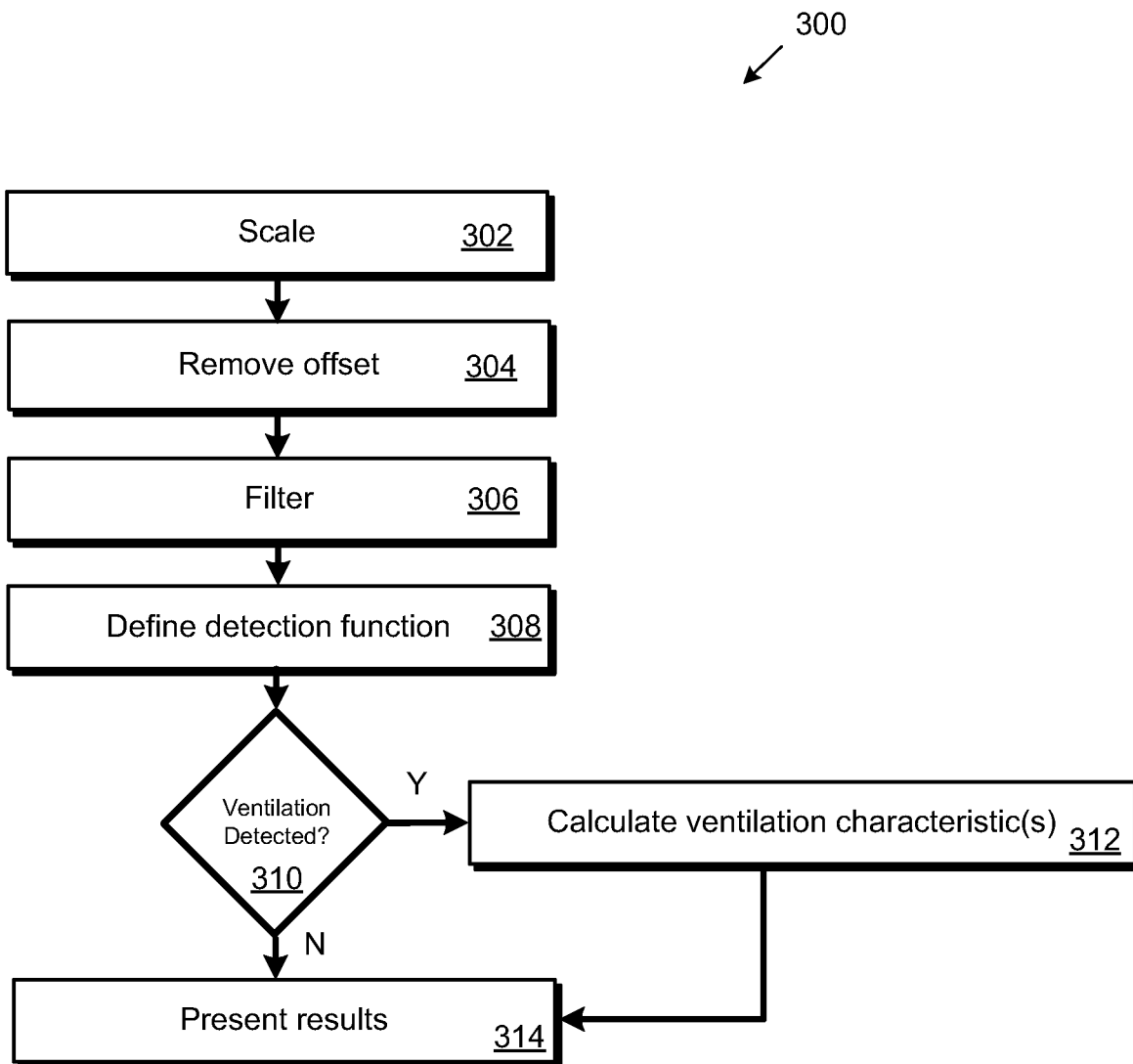
FIG. 3 is a flow chart of operations for processing signals for detecting airflow activities.

Referring to FIG. 3, a flowchart 300 is presented that represents operations of signal processor 210 (shown in FIG. 2) for processing an impedance signal (e.g., such as impedance signal 200 as provided from a pair of defibrillator electrodes). Once received, the impedance signal may be scaled 302. For example, the impedance values may be scaled by one or more quantities (e.g., using the least significant bit of the discrete values) convert the signal from digital units to physical units (e.g., milli-Ohm) in preparation of the following processing operations. Once scaled, the impedance signal may be processed to substantially remove 304 any constant offset. For example, a smoothed version of the impedance signal (e.g., a low pass filtered version of the impedance signal) may be subtracted from the originally scaled impedance signal. Along with removing offset, such processing generally removes the low frequency baseline wander from the impedance signal.

After processing the impedance signal for offset removal, the signal is filtered 306 to focus subsequent processing on the spectral portion of the signal that represents airflow activities such as ventilating a patient. One or more techniques or methodologies may be implemented for filtering the impedance signal to produce a signal that retains this spectral portion while removing energy of the spectrum external to the portion of interest. For example, by applying low pass and high pass filters to the impedance signal, the spectral portion of interest may be substantially isolated for further processing by the signal processor. Further, by using information (e.g., motion characteristics) provided by the chest compression signal, parameters for one or more of the filters may be defined and modified such that energy associated with the chest compressions is removed from the impedance signal. In one filtering arrangement, first a low pass filter is applied to the impedance signal. In general, the frequency of chest compression is larger than the frequency of ventilation cycles (or other types of airflow activities). As such, the spectral content from the chest compressions may be significantly reduced by applying a low pass filter with a cutoff frequency located below the chest compression spectral region of the signal (and located above the spectral region of the ventilations). For example, the chest compression signal may provide a compression rate of 80 to 120 compressions per minute which correspond to a frequency range of 1.33 Hz to 2.0 Hz. Airflow activities such as ventilations occur at approximately 6 to 10 instances per minute, which corresponds to a frequency range of 0.1 Hz to 0.166 Hz. Based on the chest compression signal, a cutoff frequency (e.g., to 0.5 Hz) for the low pass filter may be set such that spectral content of ventilations fall into the pass band of the filter while spectral content due to the chest compressions may be substantially removed from the signal. Various types of filters and filtering techniques (e.g., single stage, multi-stage filters) may be used to implement the low pass filter. For example, a 4th-order Butterworth filter may be implemented to provide a low pass filter for processing the impedance signal.

After applying a low pass filter to substantially remove the spectral content of the chest compression signal, the processed impedance signal may be further filtered to isolate the spectral content of the ventilations (or other type of airflow activity of the patient). For example, a high pass filter may be applied for removing spectral content of the signal located at frequencies below the spectral region of the ventilations. In one implementation, the high pass filter may be achieved in a two-step operation by first low pass filtering the impedance signal and then subtracting the resulting signal from the impedance signal. In other words, first identifying the low frequency spectral content to be removed from the impedance signal (i.e., by low pass filtering the signal), and second subtracting this identified low frequency spectral content from the impedance signal. By applying such a high pass filter after applying a low pass filter, the spectral region of interest (associated with the ventilations) can be considered isolated for additional processing (e.g., defining individual ventilations applied to the victim, determining a ventilation rate, etc.).

After filtering the impedance signal, the signal processor may define 308 a detection function from the filtered signal. In general, since the filtered impedance signal may still have noisy artifacts, threshold values can be defined to assist in identifying individual ventilation cycles (e.g., lungs inflating to initiate a ventilation cycle, lungs deflating at the end of the cycle, etc.) or other types of airflow activity events. Similar to selecting filtering parameters, threshold values may depend upon information (e.g., motion characteristics) determined from the chest compression signal 206 (shown in FIG. 2). For example, one set of thresholds may be used if chest compressions are represented in chest compression signal while another set of thresholds may be used if there appears to be no chest compressions being applied to the patient (as represented by the chest compression signal).

Figure 4A:
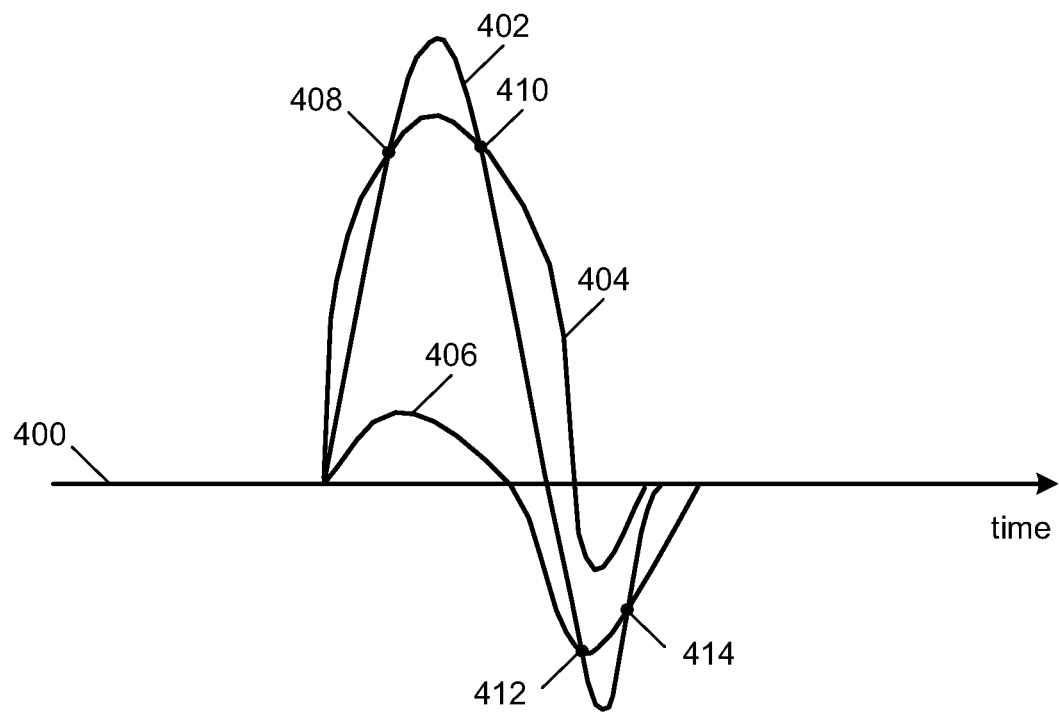
FIGS. 4a and b illustrate the processing of signals for detecting an airflow activity of a patient.

Referring to FIG. 4a, three signals are presented for demonstrating one technique of defining and using thresholds to identify a ventilation cycle (or other type of airflow activity). In the illustration, an arrowed line 400 represents increasing time for the viewer's left to right. For ease of viewing, a portion of a filtered impedance signal 402 is presented that generally increases with positive amplitude and then decreases into negative amplitude values with the passage of time.

One or more techniques may be implemented for defining thresholds to identify ventilations. For example, first a baseline threshold signal may be calculated by further filtering the filtered impedance signal 402. In one arrangement, a finite impulse response (FIR) filter may apply a low pass filter (e.g., with a cutoff frequency of 0.3 Hz) to the filtered impedance signal to produce baseline threshold signal. In some implementations, operations may be executed (e.g., by the signal processor 210) to take corrective action due to using an FIR filter. For example, an FIR filter may induce a phase shift in the signal being filtered. By storing the signal in a buffer (or other type of memory store), retrieval of the signal (e.g., by the signal processor 210) may be delayed from the buffer to induce a corrective phase shift.

Once the baseline threshold signal is produced, positive and negative threshold signals may be produced for application to the filtered impedance signal 402. One or more techniques may be implemented for defining such signals. For example, a constant value such as the maximum value of the filtered impedance signal over a period of time (e.g., the current portion of the filtered impedance signal and the previous five seconds of the filtered impedance signal) may be added to the baseline threshold signal. Next, the values of the resulting signal may be divided by a constant value (e.g., a value of two) to produce a positive threshold signal 404. Similarly, a negative threshold signal 406 may be produced by identifying a constant value such as the minimum value (i.e., a negative value) of the filtered impedance signal over a period of time (e.g., the same time period used to produce the positive threshold signal) and added to the baseline threshold signal. Also similar to the positive threshold signal, the resulting signal may be divided by a constant (e.g., the same value of two) to produce the negative threshold signal 406.

Figure 4B:
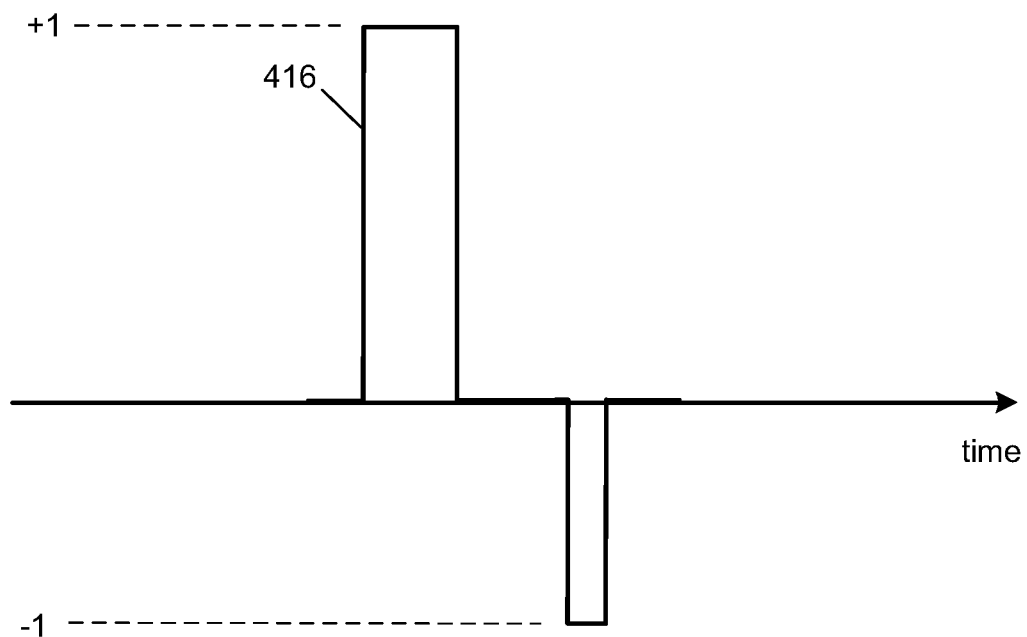

With the positive and negative threshold signals 404, 406 produced, ventilations may be identified from the filtered impedance signal 402. For example a ventilation may be identified from instances when the filtered impedance signal exceeds the positive threshold signal. In this example, points 408 and 410 identify such locations in which the filtered impedance signal 402 exceeds the positive threshold signal 404. In a similar manner, points 412 and 414 identify locations in which the filtered impedance signal 402 has drops below the negative values of the negative threshold signal 406. Referring to FIG. 4b, from the detected points 408, 410, 412, 414 a corresponding detection function 416 is produced (e.g., by the signal processor 210) in which a constant value (e.g., +1) is assigned to time instances when the filtered impedance signal exceeded the positive threshold signal 404, and, a different constant value (e.g., −1) is assigned to time instances when the filtered impedance signal falls below the negative threshold signal 406. For time instances when the filtered impedance signal falls between the threshold signals, another constant value is assigned (e.g., a value of 0).

Returning to the flowchart 300 presented in FIG. 3, after defining the detection function, the signal processor 210 may determine 310 if a ventilation (or other type of airflow activity) has occurred. One or more techniques may be implemented for such determinations, for example, one or more rules may be used in concert with the detection function. For example, one rule for defining a ventilation may call for the detection function to have a value of "+1", followed by a value of "0", followed by a value of "−1", followed by a value "0". If such a sequence of values is identified, the signal processor 210 may determine that a ventilation has occurred. Time based rules may also factor into determining if a ventilation has occurred. For example, if the sequence of values (e.g., "+1" follow by "0" "−1" and another "0") occurs over a period of time that is less than a predefined amount (e.g., 0.9 second) or greater than another predefined amount (e.g., 20 seconds), the sequence is typically considered a non-detection (e.g., noise). Other types of rules may also be defined for determining if an airflow activity has occurred. For example, rather than detecting ventilations, rules may be defined for detecting respiratory activity (e.g., the patient inhaling and exhaling unassisted).

If determined that one or more ventilations (or other types of airflow activities) have occurred, the signal processor 210 may calculate 312 characteristics of the ventilation or ventilations. For example, the time length of individual ventilations may be calculated. Time periods between ventilations may also be determined, for example, by determining the time difference between the detection of two peak values present in the detection function. If determined that a ventilation has not occurred, or after calculating any ventilation characteristic(s), the signal processor may present 314 results from the attained information. For example, along with presenting that one or more ventilation have occurred, the signal processor 210 may use this information to determine if ventilations are being appropriately applied (e.g., determine if a ventilation rate threshold has been exceeded). If ventilations are being improperly applied, the signal processor 210 may initiate an alert signal (e.g., the audible signal 212) indicating the caregiver's ventilation technique is flawed and may provide corrective instructions (e.g., inform the caregiver that the ventilation rate should be slowed).

Figure 5:
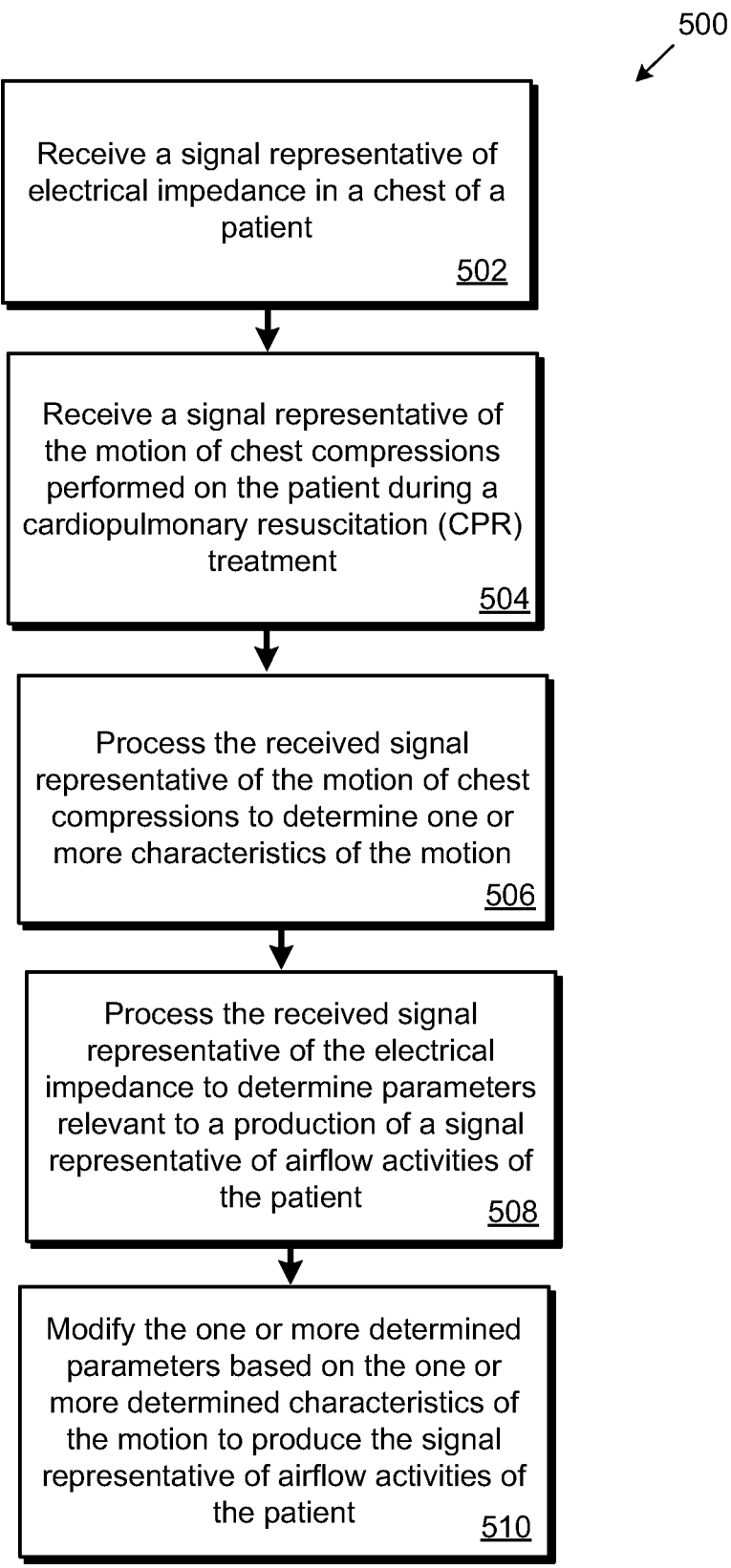
FIG. 5 is a flow chart of operations for processing signals for detecting airflow activities.

Referring to FIG. 5, a flowchart 500 represents operations of a signal processor (e.g., the signal processor 210 shown in FIG. 2). Operations of the signal processor are typically executed by a single computing device such as a defibrillator (e.g., the AED 108), a component of an electronic defibrillating system, etc. However, the operations may also be executed on other types of computing devices such as other kinds of emergency equipment. Operations of the signal processor may also be executed by multiple computing devices (e.g., multiple AEDs, an AED and a server, etc.). Along with being executed at a single site (e.g., the site of a medical emergency), execution of operations may be distributed among two or more locations (e.g., the site of the emergency and a medical facility).

Operations of the signal processor may include receiving 502 a signal representative of electrical impedance in a chest of a patient. For example, a signal may be received from a pair of defibrillator electrode pads applied to the chest of a patient during a medical emergency. Operations may also include receiving 504 a signal representative of the motion of chest compressions performed on the patient during a CPR treatment. For example, one or more motion sensing devices (e.g., an accelerometer, pressure sensor, etc.) may be implemented to provide a signal representative of the compressions. Operations may also include processing 506 the received signal representative of the motion of chest compressions to determine one or more characteristics of the motion. For example, compression depth, time, rate, etc. may be determined from the chest compression signal. Operations may also include processing 508 the received signal representative of the electrical impedance to determine parameters relevant to a production of a signal representative of airflow activities of the patient. For example, filter coefficients, cut off frequencies, threshold values, etc. may be determined for processing the impedance signal. Operations may also include modifying 510 the one or more determined parameters based on the one or more determined characteristics of the motion to produce the signal representative of airflow activities of the patient. For example, after one or more parameters (e.g., cutoff frequencies, etc.) are modified (e.g., values adjusted) based on the motion characteristics (e.g., compression rate, etc.), the impedance signal may be filtered one or more times (and in some implementations, in an adaptive manner) to substantially remove signal artifacts caused by the chest compressions and embedded in the impedance signal. One or more thresholds may also be modified and applied to impedance signal to further reduce the influencing effects of the chest compressions and to provide an accurate detection of ventilations applied to the patient during CPR. Once the ventilations or other type of airflow activities are detected, analysis operations may be executed to expose improper CPR treatment techniques (e.g., excessive ventilation cycles) and possibly suggest corrective action (e.g., alert the caregiver to slow the ventilation cycles).

Figure 6:
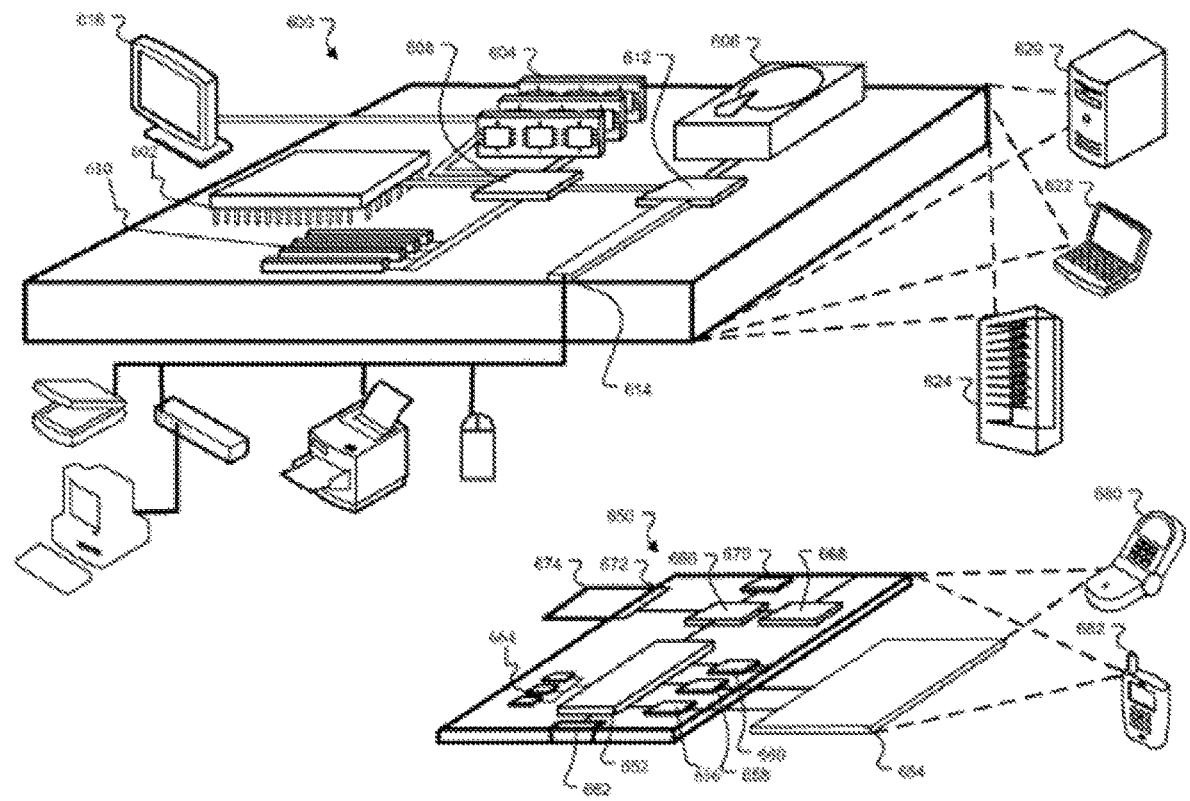
FIG. 6 shows an example of a generic computer device and a generic mobile computer device, which may be used with the techniques described here.

FIG. 6 shows an example of example computer device 600 and example mobile computer device 650, which can be used to implement the techniques described herein. For example, a portion or all of the operations of the signal processor 210 (shown in FIG. 2) for processing impedance and chest compression signals may be executed by the computer device 600 and/or the mobile computer device 650. Computing device 600 is intended to represent various forms of digital computers, including, e.g., laptops, desktops, workstations, personal digital assistants, servers, blade servers, mainframes, and other appropriate computers. Computing device 650 is intended to represent various forms of mobile devices, including, e.g., personal digital assistants, tablet computing devices, cellular telephones, smartphones, and other similar computing devices. The components shown here, their connections and relationships, and their functions, are meant to be examples only, and are not meant to limit implementations of the techniques described and/or claimed in this document.

Computing device 600 includes processor 602, memory 604, storage device 606, high-speed interface 608 connecting to memory 604 and high-speed expansion ports 610, and low speed interface 612 connecting to low speed bus 614 and storage device 606. Each of components 602, 604, 606, 608, 610, and 612, are interconnected using various busses, and can be mounted on a common motherboard or in other manners as appropriate. Processor 602 can process instructions for execution within computing device 600, including instructions stored in memory 604 or on storage device 606 to display graphical data for a GUI on an external input/output device, including, e.g., display 616 coupled to high speed interface 608. In other implementations, multiple processors and/or multiple buses can be used, as appropriate, along with multiple memories and types of memory. Also, multiple computing devices 600 can be connected, with each device providing portions of the necessary operations (e.g., as a server bank, a group of blade servers, or a multi-processor system).

Memory 604 stores data within computing device 600. In one implementation, memory 604 is a volatile memory unit or units. In another implementation, memory 604 is a non-volatile memory unit or units. Memory 604 also can be another form of computer-readable medium, including, e.g., a magnetic or optical disk. Memory 604 may be non-transitory.

Storage device 606 is capable of providing mass storage for computing device 600. In one implementation, storage device 606 can be or contain a computer-readable medium, including, e.g., a floppy disk device, a hard disk device, an optical disk device, or a tape device, a flash memory or other similar solid state memory device, or an array of devices, including devices in a storage area network or other configurations. A computer program product can be tangibly embodied in a data carrier. The computer program product also can contain instructions that, when executed, perform one or more methods, including, e.g., those described above. The data carrier is a computer- or machine-readable medium, including, e.g., memory 604, storage device 606, memory on processor 602, and the like.

High-speed controller 608 manages bandwidth-intensive operations for computing device 600, while low speed controller 612 manages lower bandwidth-intensive operations. Such allocation of functions is an example only. In one implementation, high-speed controller 608 is coupled to memory 604, display 616 (e.g., through a graphics processor or accelerator), and to high-speed expansion ports 610, which can accept various expansion cards (not shown). In the implementation, low-speed controller 612 is coupled to storage device 606 and low-speed expansion port 614. The low-speed expansion port, which can include various communication ports (e.g., USB, Bluetooth®, Ethernet, wireless Ethernet), can be coupled to one or more input/output devices, including, e.g., a keyboard, a pointing device, a scanner, or a networking device including, e.g., a switch or router, e.g., through a network adapter.

Computing device 600 can be implemented in a number of different forms, as shown in the figure. For example, it can be implemented as standard server 620, or multiple times in a group of such servers. It also can be implemented as part of rack server system 624. In addition or as an alternative, it can be implemented in a personal computer including, e.g., laptop computer 622. In some examples, components from computing device 600 can be combined with other components in a mobile device (not shown), including, e.g., device 650. Each of such devices can contain one or more of computing device 600, 650, and an entire system can be made up of multiple computing devices 600, 650 communicating with each other.

Computing device 650 includes processor 652, memory 664, an input/output device including, e.g., display 654, communication interface 666, and transceiver 668, among other components. Device 650 also can be provided with a storage device, including, e.g., a microdrive or other device, to provide additional storage. Each of components 650, 652, 664, 654, 666, and 668, are interconnected using various buses, and several of the components can be mounted on a common motherboard or in other manners as appropriate.

Processor 652 can execute instructions within computing device 650, including instructions stored in memory 664. The processor can be implemented as a chipset of chips that include separate and multiple analog and digital processors. The processor can provide, for example, for coordination of the other components of device 650, including, e.g., control of user interfaces, applications run by device 650, and wireless communication by device 650.

Processor 652 can communicate with a user through control interface 658 and display interface 656 coupled to display 654. Display 654 can be, for example, a TFT LCD (Thin-Film-Transistor Liquid Crystal Display) or an OLED (Organic Light Emitting Diode) display, or other appropriate display technology. Display interface 656 can comprise appropriate circuitry for driving display 654 to present graphical and other data to a user. Control interface 658 can receive commands from a user and convert them for submission to processor 652. In addition, external interface 662 can communicate with processor 652, so as to enable near area communication of device 650 with other devices. External interface 662 can provide, for example, for wired communication in some implementations, or for wireless communication in other implementations, and multiple interfaces also can be used.

Memory 664 stores data within computing device 650. Memory 664 can be implemented as one or more of a computer-readable medium or media, a volatile memory unit or units, or a non-volatile memory unit or units. Expansion memory 674 also can be provided and connected to device 650 through expansion interface 672, which can include, for example, a SIMM (Single In Line Memory Module) card interface. Such expansion memory 674 can provide extra storage space for device 650, or also can store applications or other data for device 650. Specifically, expansion memory 674 can include instructions to carry out or supplement the processes described above, and can include secure data also. Thus, for example, expansion memory 674 can be provided as a security module for device 650, and can be programmed with instructions that permit secure use of device 650. In addition, secure applications can be provided through the SIMM cards, along with additional data, including, e.g., placing identifying data on the SIMM card in a non-hackable manner.

The memory can include, for example, flash memory and/or NVRAM memory, as discussed below. In one implementation, a computer program product is tangibly embodied in a data carrier. The computer program product contains instructions that, when executed, perform one or more methods, including, e.g., those described above. The data carrier is a computer- or machine-readable medium, including, e.g., memory 664, expansion memory 674, and/or memory on processor 652, which can be received, for example, over transceiver 668 or external interface 662.

Device 650 can communicate wirelessly through communication interface 666, which can include digital signal processing circuitry where necessary. Communication interface 666 can provide for communications under various modes or protocols, including, e.g., GSM voice calls, SMS, EMS, or MMS messaging, CDMA, TDMA, PDC, WCDMA, CDMA2000, or GPRS, among others. Such communication can occur, for example, through radio-frequency transceiver 668. In addition, short-range communication can occur, including, e.g., using a Bluetooth®, WiFi, or other such transceiver (not shown). In addition, GPS (Global Positioning System) receiver module 670 can provide additional navigation- and location-related wireless data to device 650, which can be used as appropriate by applications running on device 650. Sensors and modules such as cameras, microphones, compasses, accelerators (for orientation sensing), etc. maybe included in the device.

Device 650 also can communicate audibly using audio codec 660, which can receive spoken data from a user and convert it to usable digital data. Audio codec 660 can likewise generate audible sound for a user, including, e.g., through a speaker, e.g., in a handset of device 650. Such sound can include sound from voice telephone calls, can include recorded sound (e.g., voice messages, music files, and the like) and also can include sound generated by applications operating on device 650.

Computing device 650 can be implemented in a number of different forms, as shown in the figure. For example, it can be implemented as cellular telephone 680. It also can be implemented as part of smartphone 682, personal digital assistant, or other similar mobile device.

Various implementations of the systems and techniques described here can be realized in digital electronic circuitry, integrated circuitry, specially designed ASICs (application specific integrated circuits), computer hardware, firmware, software, and/or combinations thereof. These various implementations can include implementation in one or more computer programs that are executable and/or interpretable on a programmable system including at least one programmable processor, which can be special or general purpose, coupled to receive data and instructions from, and to transmit data and instructions to, a storage system, at least one input device, and at least one output device.

These computer programs (also known as programs, software, software applications or code) include machine instructions for a programmable processor, and can be implemented in a high-level procedural and/or object-oriented programming language, and/or in assembly/machine language. As used herein, the terms machine-readable medium and computer-readable medium refer to a computer program product, apparatus and/or device (e.g., magnetic discs, optical disks, memory, Programmable Logic Devices (PLDs)) used to provide machine instructions and/or data to a programmable processor, including a machine-readable medium that receives machine instructions.

To provide for interaction with a user, the systems and techniques described here can be implemented on a computer having a display device (e.g., a CRT (cathode ray tube) or LCD (liquid crystal display) monitor) for displaying data to the user and a keyboard and a pointing device (e.g., a mouse or a trackball) by which the user can provide input to the computer. Other kinds of devices can be used to provide for interaction with a user as well; for example, feedback provided to the user can be a form of sensory feedback (e.g., visual feedback, auditory feedback, or tactile feedback); and input from the user can be received in a form, including acoustic, speech, or tactile input.

The systems and techniques described here can be implemented in a computing system that includes a back end component (e.g., as a data server), or that includes a middleware component (e.g., an application server), or that includes a front end component (e.g., a client computer having a user interface or a Web browser through which a user can interact with an implementation of the systems and techniques described here), or a combination of such back end, middleware, or front end components. The components of the system can be interconnected by a form or medium of digital data communication (e.g., a communication network). Examples of communication networks include a local area network (LAN), a wide area network (WAN), and the Internet.

The computing system can include clients and servers. A client and server are generally remote from each other and typically interact through a communication network. The relationship of client and server arises by virtue of computer programs running on the respective computers and having a client-server relationship to each other.

In some implementations, the engines described herein can be separated, combined or incorporated into a single or combined engine. The engines depicted in the figures are not intended to limit the systems described here to the software architectures shown in the figures.

A number of embodiments have been described. Nevertheless, it will be understood that various modifications can be made without departing from the spirit and scope of the processes and techniques described herein. In addition, the logic flows depicted in the figures do not require the particular order shown, or sequential order, to achieve desirable results. In addition, other steps can be provided, or steps can be eliminated, from the described flows, and other components can be added to, or removed from, the described systems. Accordingly, other embodiments are within the scope of the following claims.

What is claimed is:

1. An apparatus for assisting ventilations provided to a patient, the apparatus comprising:
   a plurality of electrodes configured to provide signals representative of airflow activities of the patient, the signals comprising electrical impedance signals measured across the patient's chest and indicative of changes to the patient's chest geometry;
   one or more chest compression sensors configured to provide signals representative of chest displacement due to chest compressions;
   a processor and a memory configured to:
      receive the signals representative of the airflow activities of the patient from the plurality of electrodes,
      receive the signals representative of chest displacement due to chest compressions from the one or more chest compression sensors,
      identify a presence of chest compressions applied to the patient based on the signals representative of chest displacement,
      subsequent to identification of the presence of chest compressions, confirm an absence of chest compressions applied to the patient based on the signals representative of chest displacement,
      for the signals representative of the airflow activities of the patient, adjust one or more signal processing parameters from a first set of threshold values to a second set of threshold values in response to the confirmed absence of chest compressions applied to the patient, the one or more signal processing parameters comprising at least the first set of threshold values which are for use in processing the electrical impedance signals in the presence of chest compressions applied to the patient and the second set of thresholds which are for use in the absence of chest compressions applied to the patient, and
      process the signals representative of the airflow activities of the patient using the adjusted one or more signal processing parameters to determine feedback for providing the ventilations to the patient in the absence of chest compressions; and
   an output device coupled to the processor and the memory and configured to provide the feedback for providing the ventilations to the patient.

2. The apparatus of claim 1, wherein the one or more signal processing parameters comprise signal filters.

3. The apparatus of claim 1, wherein the processor is configured to:
   identify a period of time associated with the absence of chest compressions, and
   change the one or more signal processing parameters when the period of time reaches a predetermined value.

4. The apparatus of claim 3, wherein the predetermined value is 1-5 seconds.

5. The apparatus of claim 1, wherein the processor is configured to:
   identify a resumption of chest compressions based on the signals representative of chest displacement, and
   change the one or more signal processing parameters in response to the identified resumption of chest compressions.

6. The apparatus of claim 1, wherein the plurality of electrodes comprise electrocardiogram (ECG) electrodes.

7. The apparatus of claim 1,
   wherein the plurality of electrodes are configured to couple to a defibrillator, and
   wherein the processor, the memory, and the output device are disposed in the defibrillator.

8. The apparatus of claim 1, wherein the one or more chest compression sensors comprise an accelerometer assembly configured to move with the patient's chest and a caregiver's hands.

9. The apparatus of claim 8, wherein the signals representative of chest displacement comprise acceleration signals.

10. The apparatus of claim 9, wherein the processor is configured to doubly integrate the acceleration signals and determine chest displacement from the doubly integrated acceleration signals.

11. The apparatus of claim 1, wherein the airflow activities comprise patient respiration or patient ventilation.

12. The apparatus of claim 1, wherein the feedback comprises one or more of visible feedback and audible feedback.

13. The apparatus of claim 1, wherein the feedback for adjusting the ventilations of the patient includes cardiopulmonary resuscitation instructions.

14. The apparatus of claim 1, wherein the signals representative of the airflow activities of the patient indicate over ventilation of the patient.

15. The apparatus of claim 14, wherein the feedback for adjusting the ventilations comprises an instruction to reduce a ventilation frequency.

* * * * *